United States Patent [19]

Jones

[11] 4,123,397

[45] Oct. 31, 1978

[54] AGGLOMERATION OF STARCH-HYDROLYZED POLYACRYLONITRILE GRAFT COPOLYMER

[75] Inventor: Duane A. Jones, Minneapolis, Minn.

[73] Assignee: General Mills Chemicals, Inc., Minneapolis, Minn.

[21] Appl. No.: 806,641

[22] Filed: Jun. 15, 1977

[51] Int. Cl.² ............................................. C08L 3/02
[52] U.S. Cl. .................... 260/17.4 GC; 47/DIG. 10; 128/284; 128/285; 128/290 R; 128/296
[58] Field of Search ................ 260/17.4 ST, 17.4 GC

[56] References Cited

U.S. PATENT DOCUMENTS

| | | | |
|---|---|---|---|
| 3,985,616 | 10/1976 | Weaver et al. | 260/17.4 GC |
| 3,995,998 | 12/1976 | Rowland et al. | 260/17.4 GC |
| 3,997,484 | 12/1976 | Weaver et al. | 260/17.4 ST |
| 4,026,849 | 5/1977 | Bagley et al. | 260/17.4 ST |
| 4,069,177 | 1/1978 | Smith | 260/17.4 GC |

OTHER PUBLICATIONS

Chem. Absts., vol. 65: 9150f, Graft Co-polymers of Starch, Fanta et al.
Chem. Absts., vol. 82: 18122u, Pulverized Resin Compositions, Yamanouchi.

*Primary Examiner*—Edward M. Woodberry
*Attorney, Agent, or Firm*—Elizabeth Tweedy; Patrick J. Span

[57] ABSTRACT

A method of agglomerating and desolventizing starch-hydrolyzed polyacrylonitrile graft copolymer using atomized, liquid water.

3 Claims, No Drawings

AGGLOMERATION OF STARCH-HYDROLYZED POLYACRYLONITRILE GRAFT COPOLYMER

This invention relates to a process for agglomerating and desolventizing particles of starch-hydrolyzed polyacrylonitrile graft copolymer. More especially, this invention relates to a process of agglomerating and desolventizing particles of starch-hydrolyzed polyacrylonitrile graft copolymer which does not reduce its fluid absorbency.

SUMMARY OF INVENTION

The process of this invention comprises wetting particles of starch-hydrolyzed polyacrylonitrile graft copolymer during mixing with atomized, liquid water until a moisture content of the particles reaches about 17 to 22% by weight based upon the weight of the total composition and subsequently drying the particles at a temperature of about 25° C. to 100° C. to a moisture content of about 3% to 12.5% by weight of the total composition and preferably about 7.5% to 12.5% by weight of the total composition for optimum dispersability. Agglomeration by this method does not decrease the fluid absorbency of the copolymer. In addition, alcohol solvents containing one to three carbon atoms commonly used in purifying the copolymer are released during the process without adversely affecting the copolymer's fluid absorbency.

BACKGROUND OF INVENTION

Starch-hydrolyzed polyacrylonitrile graft copolymers exhibiting the capacity to absorb from about 300 to 1,000 times their weight of deionized water are known at this time. The development of these compositions was carried out by the Northern Regional Research Laboratory, Peoria, Illinois. The starch-hydrolyzed polyacrylonitrile graft copolymer is produced by exposure of starch, either gelatinized or ungelatinized, to cerium salt, such as cerium ammonium nitrate, which acts as a catalyst to generate free radicals. Polyacrylonitrile chains form at the site of these free radicals. The resulting material is then saponified in sodium hydroxide to hydrolyze the polyacrylonitrile chains to carboxamide and alkali metal carboxylate groups mixed with metal salts. After drying, the material can absorb about 300 to 400 times its weight. Drying can be accomplished by drum, tumble air or vacuum drying. Extraction of the copolymer dispersion with alcohol before drying provides a material with fluid absorbency of 800 to 1,000 times its weight. The fluid absorbency is determined by suspending a weighed amount of dry copolymer in an excess of testing fluid and filtering to recover unabsorbed fluid.

The copolymer can be made as film, flakes, powder or mat. These forms take up water, swelling but not dissolving, and hold it in expanded duplications of their own dry shapes. Films extend and thicken to sheets. Powders become piles of water textured like crushed ice. A flake expands to a clear, angular piece of water. The swollen forms shrink in dilute acid and expand again in dilute alkali solution. They also shrink as they dry and expand again with water.

The copolymer, with these properties, can be mixed with or coated on a wide variety of materials including, for example, sand, straw, sawdust, seeds and roots, natural or synthetic fibers, and flour, gelatin and starch. It can hold water in soils, animal bedding and kitty litter, toweling and diapers, bandages, surgical pads and dental absorbents.

The copolymer, as commercially produced, is a granular powder. The powder varies in granulation, typically from 30 mesh to 400 mesh U.S. Standard Sieve. Fine powders such as those having granulation of 200 mesh to 325 mesh U.S. Standard Sieve, and especially those having a granulation of less than 325 mesh U.S. Standard Sieve, are not as generally useful as coarser granulations because they are harder to apply, harder to contain and, in some instances, they do not disperse or wet-out as well as the coarser particles. Finer granulations can be mechanically separated from the coarser. With respect to economics and material conservation, however, the finer material must be used in some manner.

A further disadvantage of the commercial product is the solvent content. Some alcohol residues are normally retained in the product upon drying. It is known that alcohol solvents used in purification of starch alone can be removed by passing gaseous water or humidified air through particles of the starch and, thereafter, drying the particles. Unfortunately, the fluid absorbency of the copolymer of this invention is adversely affected by these processes. The results of desolventizing with gaseous water or humidified air are shown in Examples I and II. In the past, therefore, there has been a problem in producing low alcohol content, high fluid absorbent copolymers suitable for uses in which alcohols could not be tolerated.

DETAILS OF THE INVENTION

It has now been found that particles of starch-hydrolyzed polyacrylonitrile graft copolymer can be agglomerated by adding atomized, liquid water, mixing and, thereafter, drying. One unexpected result of this process is that trace levels of the process solvents, namely alcohols, remaining in the product after manufacture, typically in an amount of from about 0.5% to 2.5% by weight of the total composition, were significantly reduced during the process to levels of about 0.10% by weight or less without adversely affecting the fluid absorbency of the material.

The process of the present invention is useful in converting fine particles to useful material. It is also useful in producing high fluid absorbent copolymer for applications in which alcohol in significant levels can not be tolerated.

The atomized, liquid water spray or stream can be supplied through an aspirator or atomizer. It is essentially a fine spray of liquid water.

Preferably the mixing of the copolymer particles during the process is carried out by tumbling the particles. This permits the particles to be exposed to the atomized, liquid water spray or stream as well as with each other. Alternatively, the particles could be mixed in a fluid bed or some other mixing arrangement which permits uniform distribution of the water and contact with other copolymer particles.

Drying of the wetted or dampened particles can be carried out at a temperature between about 25° C. and 100° C. Best results were obtained at temperatures of about 40° C. to 80° C. Drying can be carried out in forced-air drying ovens or in vacuum ovens. It was found that a product which contained about 17% by weight water dried at a temperature of about 40° C. in a period of about 16 hours.

Set out below are specific examples illustrating the invention and comparing the results obtained from the practice of the invention with the results obtained from other possible methods of agglomeration investigated. These specific examples are presented for purposes of illustration and not as limiting the scope of the invention.

EFFECT OF HUMIDIFIED AIR UPON COPOLYMER

Example I

A series of samples of copolymer were exposed to humidified air at different temperatures to determine if the copolymer could be agglomerated and/or desolventized by that method. The samples initially contained 3.3% by weight methanol and 5.7% by weight water and exhibited a fluid absorbency of 83.0-85.0 grams of 1% by weight sodium chloride solution per gram of copolymer. It was found that, in order to effect desolventization, a relative humidity of 37% or greater was necessary. The results of the above series of tests are shown in Table 1. These results show that the samples which exhibited desolventization exhibited reduced fluid absorbency in 1% by weight sodium chloride solution.

Table 1

| RELATIVE HUMIDITY %[1] | TEMP. °C. | % METHANOL (GLC) | % MOISTURE (Calc.) | ABSORBENCY 1% NaCl g/g[2] |
|---|---|---|---|---|
| 58.3 | 21 | <0.1 | 30.7 | 43.6 |
|  | 40 | <0.1 | 28.9 | 42.0 |
|  | 51 | <0.1 | 28.2 | 39.6 |
| 47.2 | 21 | <0.1 | 23.6 | 62.0 |
|  | 40 | <0.1 | 21.8 | 60.0 |
|  | 51 | <0.1 | 21.2 | 62.2 |
| 37.1 | 21 | <0.1 | 17.6 | 77.8 |
|  | 40 | <0.1 | 15.6 | 77.8 |
|  | 51 | <0.1 | 14.9 | 80.6 |
| 18.8 | 21 | 1.9 | 10.6 | 80.8 |
|  | 40 | 0.9 | 10.3 | 76.6 |
|  | 51 | 0.8 | 10.0 | 86.4 |
| 8.5 | 21 | 2.9 | 6.3 | 81.8 |
|  | 40 | 2.4 | 6.2 | 80.2 |
|  | 51 | 2.4 | 5.8 | 85.6 |
| 3.2 | 21 | 2.8 | 4.9 | 80.6 |
|  | 40 | 2.7 | 3.9 | 76.2 |
|  | 51 | 2.8 | 3.5 | 86.6 |
| Control | — | — | — | 83.0-85.0 |

[1]Exposure time 24 hours
[2]After drying at 40° C. under vacuum for 16 hours

Example II

Using the procedure set out in Example I, a series of copolymer samples containing 33% by weight methanol and 6.4% by weight water were exposed to air streams having relative humidities of 38% or 48% and a temperature of 40° C. The results are shown in Table 2.

Table 2

| Exposed to Humidified Air Time/Hours | 38% Relative Humidity | | |
|---|---|---|---|
|  | % Methanol (GLC) | % Moist.[1] | Absorbency 1% NaCl, g/g[2] |
| ½ | 7.5 | 14.7 | 48.8 |
| 1 | 1.4 | 16.0 | 45.6 |
| 2 | 0.50 | 14.6 | 50.4 |
| 3 | 0.38 | 12.3 | 48.6 |
| 4 | 0.34 | 12.3 | 47.8 |
| 8 | 0.17 | 12.1 | — |
| 16 | 0.16 | 12.1 | — |
| Oven Dried Control | 3.3 | 5.7 | 51.0-53.4 |
| Exposed to Humidified Air | 48% Relative Humidity | | |
|  | % Methanol | % Moist. | Absorbency |

Table 2-continued

| Time/Hours | (GLC) | Moist.[1] | 1% NaCl, g/g[2] |
|---|---|---|---|
| ½ | 3.3 | 16.9 | 49.2 |
| 1 | 0.54 | 18.1 | 49.6 |
| 2 | 0.13 | 19.1 | 44.8 |
| 3 | 0.12 | 17.9 | 44.0 |
| 4 | 0.08 | 16.4 | 44.0 |
| 8 | — | — | — |
| 16 | — | — | — |
| Oven Dried Control | 3.3 | 5.7 | 51.0-53.4 |

[1]Analyzed by Karl Fisher procedure
[2]After drying at 40° C. for 16 hours

AGGLOMERATION WITH ATOMIZED LIQUID WATER

Example III

Dry copolymer powder having the following analyses and granulations
Moisture: 3.2%
Methanol: 1.2%
Granulations
30-100 mesh: 37.0%
100-200 mesh: 23.0%
200-325 mesh: 14.0%
−325 mesh: 25.0%
was agglomerated with 10%, 15% and 20% added water, based on total weight of the wetted copolymer, in the following manner: the powder charge was placed in an inclined cylinder, closed at the bottom, which could be rotated like a cement mixer. While revolving, water was added slowly in the form of a mist using a pressure aspirator to atomize the water. Rate of addition was controlled so as to prevent build-up of large agglomerates. After addition of water was complete, agglomerated products were transferred to trays and dried in a forced air oven at a temperature of 40°-45° C. for 16 hours. Dried product was sieve classified to determine agglomeration efficiency and GLC analyzed to determine methanol remaining in the product after water agglomeration and redrying. Results, tabulated in Table 3, show that about 17% water must be added, basis the wet agglomerated product, to reduce methanol level of final product to 0.10% methanol or below. At 20% water addition, the fine fraction (−100 mesh) of the product was halved, i.e. decreased from 73% to 37%.

Table 3

AGGLOMERATION OF POWDERED COPOLYMER WITH VARYING AMOUNTS OF WATER

| Sample | % by weight H₂O added | Product Granulation, % | | % Methanol Content |
|---|---|---|---|---|
|  |  | +100 mesh | −100 mesh |  |
| 1 | None (Control) | 37 | 73 | 1.2 |
| 2 | 10 | 55 | — | 0.75 |
|  |  | — | 45 | 0.36 |
| 3 | 15 | 64 | — | 0.36 |
|  |  | — | 36 | 0.14 |
| 4 | 20 | 73 | — | 0.10 |
|  |  | — | 37 | 0.03 |
| 5 | 25 | —* | —* | —* |

*Water addition level was too high. Product became doughy in rotary mixer and produced a non-granular, glossy solid on drying.

Example IV

Dry copolymer having the following analyses and granulations
Moisture: 6.3% by weight
Methanol: 1.2% by weight
Fluid Absorbency: 87 ml/g (1.0% NaCl solution)

Granulation
- 30 – 100 mesh: 19.0%
- 100 – 200 mesh: 34.0%
- 200 – 325 mesh: 22.0%
- −325 mesh: 26.0% was sieve-classified to separate into the following portions: +100 mesh, 100–140 mesh, 140–200 mesh and −200 mesh. Portions of the last three portions were agglomerated as described in Example 3 using 20% by weight water (basis the wet weight of agglomerate) and dried in the same manner. Dried products were sieve-classified to determine agglomeration efficiency, analyzed for methanol to determine degree of desolventization and evaluated for fluid absorbency to determine effect of agglomeration on product performance. Results, tabulated in Table 4, show that agglomeration of product powders ranging from fine (100–140 mesh) to very fine (−200 mesh) in the manner described here significantly increased product granulation, reduced product methanol content and did so without adversely affecting the fluid absorbency of the product.

The embodiments of the invention in which an exclusive property or privilege is claimed are defined as follows:

1. A process of agglomerating and desolventizing starch-hydrolyzed polyacrylonitrile graft copolymer wherein said acrylonitrile is hydrolyzed to carboxamide and alkali metal carboxylate groups, comprising wetting particles of starch-hydrolyzed polyacrylonitrile copolymer during mixing with atomized, liquid water until the moisture content of the particles reaches about 17% to 22% by weight based upon the weight of the total composition and subsequently drying the particles at a temperature between about 25° C. to 100° C. to a moisture content of about 3% to 12.5% by weight of the total composition.

2. The process of claim 1 wherein the drying temperature is between about 40° C. and 80° C.

3. The process of claim 1 wherein the final moisture content of the copolymer is between about 7.5% to 12.5% by weight of the total composition.

* * * * *

Table 4
AGGLOMERATION OF POWDERED COPOLYMER OF VARYING GRANULATIONS USING 20% BY WEIGHT WATER ADDED

| Sample | Powdered Granulation Before Agglomeration | Agglomerated Product | | | |
|---|---|---|---|---|---|
| | | Granulation (mesh) | | Methanol Content (%) | 1.0% NaCl Solution Absorbency |
| | | 40–80 | −80 | | |
| 1 | 100–140 | 70 | | 0.05 | — |
| | | | 30 | 0.02 | 94 |
| 2 | 140–200 | 73 | | 0.01 | — |
| | | | 37 | 0.01 | 97 |
| 3 | −200 mesh | 60 | | 0.01 | — |
| | | | 40 | 0.01 | 86 |
| Control | unclassified | — | — | 1.20 | 87 |